(12) United States Patent
Kim

(10) Patent No.: US 9,283,205 B2
(45) Date of Patent: Mar. 15, 2016

(54) METHOD FOR EXTRACTING TREATMENT INGREDIENTS FOR GASTROINTESTINAL DISEASES FROM BARK OF LIRIODENDRON TULIPIFERA

(71) Applicant: CHO DANG PHARM. CO., LTD., Seoul (KR)

(72) Inventor: Nak Doo Kim, Seoul (KR)

(73) Assignee: Cho Dang Pharm. Co., Ltd., Seoul (KR)

( * ) Notice: Subject to any disclaimer, the term of this patent is extended or adjusted under 35 U.S.C. 154(b) by 0 days.

(21) Appl. No.: 14/379,165

(22) PCT Filed: Feb. 1, 2013

(86) PCT No.: PCT/KR2013/000817
§ 371 (c)(1),
(2) Date: Aug. 15, 2014

(87) PCT Pub. No.: WO2013/122343
PCT Pub. Date: Aug. 22, 2013

(65) Prior Publication Data
US 2015/0011624 A1  Jan. 8, 2015

(30) Foreign Application Priority Data

Feb. 16, 2012  (KR) ........................ 10-2012-0015710

(51) Int. Cl.
*A01N 65/00* (2009.01)
*A61K 31/365* (2006.01)
*A61K 36/57* (2006.01)

(52) U.S. Cl.
CPC ............... *A61K 31/365* (2013.01); *A61K 36/57* (2013.01); *A61K 2236/00* (2013.01)

(58) Field of Classification Search
CPC .................................................. A61K 36/00
USPC ........................................................ 424/725
See application file for complete search history.

(56) References Cited

U.S. PATENT DOCUMENTS

| 4,093,717 A | 6/1978 | Hufford |
| 2006/0228412 A1 | 10/2006 | Clouatre et al. |
| 2015/0011622 A1 | 1/2015 | Kim |
| 2015/0011623 A1 | 1/2015 | Kim |

FOREIGN PATENT DOCUMENTS

| KR | 2000-0066932 A | 11/2000 |
| KR | 2005-0055856 A | 6/2005 |
| KR | 2010-0036052 A | 4/2010 |
| KR | 2011-0091127 A | 8/2011 |

OTHER PUBLICATIONS

CRC Ethnobotany Desk Reference, Johnson, pp. 480-481,CRC Press LLC, Boca Raton, Florida (1998). (Best available copy).
Doskotch, R.W. and El-Feraly, F.S., "Antitumor agents II: Tulipinolide, a new germacranolide sesquiterpene, and costunolide. Two cytotoxic substances from *Liriodendron tulipifera*L.," *Journal of Pharmaceutical Sciences* 58(7):877-880, Wiley-Liss, Inc., United States (1969).
Doskotch, R.W. and El-Feraly, F.S., "The structure of tulipinolide and epitulipinolide. Cytotoxic sesquiterpenes from *Liriodendron tulipifera* L.," *Journal of Organic Chemistry* 35(6):1928-1936, American Chemical Society, United States (1970).
Doskotch, R.W., et al., "New sesquiterpene lactones from *Liriodendron tulipifera*," *Photochemistry* 14(3):769-773, Elsevier Ltd., England (1975).
Sahoo, P.K., "Pharmacy, Pharmaceutical Technology, Tablets," nsdl.niscair.res.in, accessed at http://nsdl.niscair.res.in/jspui/bitstream/123456789/315/1/Tablet%20Technology%20 Edited.pdf, accessed on Dec. 1, 2015, 42 pages (2007).
Troy, D.B., et al., "Solutions and Phase Equilibria," in *Remington: The Science and Practice of Pharmacy*, vol. 1, Troy, D.B., ed., p. 229, Lippincott Williams & Wilkins, United States (2006). (Best available copy).
Wagner, H. and Wolfe, P., *New Natural Products and Plant Drugs with Pharmacological, Biological or Therapeutic Activity*, p. 161, Springer-Verlag Berlin Heidelberg, Germany (1977). (Best available copy).
International Search Report and Written Opinion for International Application No. PCT/KR2013/000817, Korean Intellectual Property Office, Republic of Korea, mailed May 29, 2013, 7 pages.
English translation of International Search Report and Written Opinion for International Application No. PCT/KR2013/000817, Korean Intellectual Property Office, Republic of Korea, mailed May 29, 2013, 8 pages.

*Primary Examiner* — Michael Meller
(74) *Attorney, Agent, or Firm* — Sterne, Kessler, Goldstein & Fox P.L.L.C.

(57) ABSTRACT

The present invention relates to a method for extracting treatment ingredients for gastrointestinal diseases from the bark of *Liriodendron tulipifera*, the treatment ingredients containing epitulipinolide and costunolide as active ingredients, and to a therapeutic agent for gastrointestinal diseases, containing epitulipinolide and costunolide extracted using said method.

2 Claims, 2 Drawing Sheets

METHOD FOR EXTRACTING TREATMENT INGREDIENTS FOR GASTROINTESTINAL DISEASES FROM BARK OF LIRIODENDRON TULIPIFERA

This is a national phase application of PCT/KR2013/000817 filed on Feb. 1, 2013, claiming priority to Korean Patent Application No. 10-2012-0015710 filed on Feb. 16, 2012, the contents of which are incorporated herein by references.

TECHNICAL FIELD

The present invention relates to a process for preparing the extract from bark of *Liriodendron tulipifera* for treating gastrointestinal disease. Further, the present invention also relates to a therapeutic agent for treating gastrointestinal disease containing epitulipinolide and costunolide extracted from bark of *Liriodendron tulipifera*

DESCRIPTION OF PRIOR ART

It has been reported that the gastritis and/or stomach ulcer is the most common disease, because about 10% of Korean populations have suffered from gastritis and/or stomach ulcer more than once in a whole life. The causes of gastritis and/or stomach ulcer have been known by the digestion of stomach wall containing mucosa, sub-mucosa, muscularis externa and serosa by gastric acid. Gastritis has been referred if only gastric mucosa has been damaged, while stomach ulcer has been referred if gastric sub-mucosa and muscularis externa have been damaged. Further, the unbalance between offensive factor and defensive factor may cause the generation of gastritis and/or stomach ulcer, for example, the increase of offensive factor or the decrease of defensive factor.

The increase of secretion of gastric acid and/or pepsin can be an example of increase of offensive factor, while the defect of gastric mucosa, the decrease of mucus secretion, the decrease of bicarbonate ion secretion and/or the decrease of prostaglandin production can be an example of decrease of defensive factor. On the other hand, it has been known that the infection of *Helicobacter pylori* can cause the gastritis and/or stomach ulcer.

Gastric acid hyper-secretion has been regarded as the main cause of gastritis and/or stomach ulcer. The gastric acid, which is hydrochloric acid secreted from stomach wall cells has a role for digesting proteins by activating pepsin as well as damaging the stomach wall. The therapeutic agent for treating gastritis and/or stomach ulcer can be classified into the drug inhibiting the offensive factor, for example, gastric acid, pepsin, smoke, oxygen free radical and/or alcohol, and the drug enhancing the defensive factor.

As an offensive factor inhibitor, antacid and/or gastric acid secretion inhibitor can be exemplified. Further, as a gastric acid secretion inhibitor, the antagonist of H2 receptor, for example, cimetidine, ranitidine and/or famotidine etc.; the proton pump inhibitor (PPI), for example, omeprazole and/or lansoprazole can be exemplified. Especially, almost 100% of duodenal ulcer and more than 90% of stomach ulcer can be initially recovered by administration of PPI drug. However, in spite of improving initial recovery rate of duodenal ulcer and/or stomach ulcer, the recurrence rate has not been reduced.

On the other hand, a defensive factor enhancer can induce the covering of the ulcerative lesion, the synthesis and secretion of mucus, the increase of blood flow in gastric mucosa, the increase of endogenous prostaglandin and/or the increase of tissue regeneration. Further, it has been known that a defensive factor enhancer has been useful for preventing the recurrence of duodenal ulcer and/or stomach ulcer. Of course, the sterile therapy of *Helicobacter pylori* also can be considered as important treating method against ulcer.

However, the causes of gastritis and/or stomach ulcer have not been clearly disclosed since complex causes result in gastritis and/or stomach ulcer. Therefore, the absolute treating method has not been developed.

On the other hand, *Liriodendron tulipifera* L. is a kind of deciduous broad-leaved arboreal belonged to Magnoliaceae family. It has been used as a raw material of pulp. In the bark, leave and/or wood of *Liriodendron tulipifera*, alkaloid, sesquiterpene and/or lignan has been known to be included.

It has been known that aporphine alkaloid having anti-bacterial activity has been contained in the bark of *Liriodendron tulipifera* (Hufford C. D. and Funderburk M. J., *J. Pharm. Sci.* 63: pp. 1338-1339, 1974; Hufford C. D. et al., *J. Pharm. Sci.* 64: pp. 789-792, 1975). Further, the bark extract containing this alkaloid has been used for treating malaria since Unites States War of Independence. On the other hand, glaucine alkaloid has been used for antitussive agent in Soviet Union.

According to the research in 1975, the alkaloid fraction extracted from the bark of *Liriodendron tulipifera* has been reported as having anti-bacterial activity. Further, it has been reported that N-methyllaurotetanine, lirioferine and/or liriotulipiferine has an anti-fungal activity (Huang Hsu, C-Y, 1976. MS thesis, North Carolina State University, Raleigh). Further, it has been also reported that dehydroglaucine and/or liriodenine has cytotoxicity and anti-bacterial activity (Warthen D, Gooden E L and Jacobson M., *J. Pharm. Sci.*, 58: pp. 637-638 (1969); Hufford C D, Funderburk M J, Morgan J M. et al., *J. Pharm. Sci.*, 64: pp. 789-792 (1975); Chen C R, Bed J L, Doskotch R W et al., *Lloydia* 37: pp. 493-500 (1974)).

On the other hand, it has been also disclosed that sesquiterpene lactone extracted from bark of *Liriodendron tulipifera* has an anti-tumor activity. Further, costunolide, tulipinolide, epi-tulipinolide, epi-tulipdienolide and/or gamma-liriodenolide has been also disclosed as an effective ingredient of the bark of *Liriodendron tulipifera* (Doskotch R. W and EL-Feraly F. S., *J Pharm. Sci.* 58: pp. 877-880, 1969; Doskotch R. W and E LI-Feraly F. S., *J. Org. Chem.* 35: pp. 1928-1936, 1970; Moon M. K. et al., *Arch. Pharm. Res.* 30: pp. 299-302, 2007).

Further, in the leaf of *Liriodendron tulipifera*, lipiferolide, epitulipinolide diepoxide and/or peroxyferolide has been also disclosed as an effective ingredient (Doskoch R W, EL-Feraly F S, Fairchild E H, *J. Chem. Soc* (Chem. Comm) pp. 402-403, 1976; Doskotch R W, EL-Feraly F S, Fairchild E H, *J. Org. Chem.* 42: pp. 3614-3618, 1977). On the other hand, in the bark of *Liriodendron tulipifera*, lignan derivatives, pinoresinol, (+)-syringaresinol and/or liriodendrin in the form of monoglycoside or diglycoside has been also disclosed as an effective ingredient (Dickey E E., *J. Org. Chem.* 23: pp. 179-184, 1958; Fujimoto H and Higuchi T., *J. Jap. Wood Res. Soc*, 23: pp. 405-410, 1977). Further, it has been reported that liriodendrin causes the bone growth in animal (Korean patent registration No. 10-597,563).

The inventor of present application has considered that extract from the bark of *Liriodendron tulipifera* containing epitulipinolide and costunolide as active ingredients can be applied for treating gastritis and/or stomach ulcer. Further, various kinds of small amount materials have been isolated in the extract composition from the bark of *Liriodendron tulipifera*.

Therefore, the inventor of present application has prepared a process for preparing the extract from the bark of *Liriodendron tulipifera* for treating gastritis and/or stomach ulcer. Finally, the present invention has been completed by developing a process for preparing the extract containing epitulipinolide and costunolide as active ingredients from the bark of *Liriodendron tulipifera* for treating gastritis and/or stomach ulcer.

Problem to be Solved

The problem to be solved is to develop an effective process for preparing the extract from the bark of *Liriodendron tulipifera* for preventing or treating gastritis and/or stomach ulcer. Accordingly, the development of effective process for preparing the extract containing epitulipinolide and costunolide as active ingredients from the bark of *Liriodendron tulipifera* has been carried out for preventing or treating gastritis and/or stomach ulcer.

Means for Solving the Problem

The object of present application is to provide a process for preparing the extract from the bark of *Liriodendron tulipifera* comprising the steps of: 1) mixing 1 wt part of chopped and dried bark of *Liriodendron tulipifera* with 2~20 wt part of ethyl acetate or dichloromethane; and 2) extracting and concentrating said mixture for 1~4 days at 15~50° C., wherein said extract comprises 0.1~10 wt % of epitulipinolide and costunolide, said extraction is made by at least one selected from enfleurage, percolation, ultra sonic, maceration or reflux.

The another object of present application is to provide a process for purifying the extract from the bark of *Liriodendron tulipifera* comprising the steps of: 1) dissolving the extract obtained in claim 1 with C1~C3 lower alcohol aqueous solution; 2) removing the lipid and water-insoluble material in the hexane layer, after adding and mixing hexane to the mixture obtained in step 1); and 3) isolating, purifying and drying the material in lower alcohol aqueous solution layer.

Further, said step 2) further comprises the step for adding water to the lower alcohol aqueous solution layer to obtain the low concentration of lower alcohol aqueous solution; the step for adding dichloromethane to obtain dichloromethane layer; and the step for isolating, purifying and drying the material in dichloromethane layer.

On the other hand, the another object of present application is to provide an extract from the bark of *Liriodendron tulipifera* containing epitulipinolide and costunolide as active ingredient obtained by according to the method described above.

The further object of present application is to provide a pharmaceutical composition for preventing or treating gastritis and/or stomach ulcer comprising the extract from the bark of *Liriodendron tulipifera*, wherein said pharmaceutical composition comprises epitulipinolide and costunolide as active ingredients.

Advantageous Effect

The outstanding advantageous effect of present application is to provide an effective process for preparing the extract from the bark of *Liriodendron tulipifera* for preventing or treating gastritis and/or stomach ulcer. Accordingly, the development of effective process for preparing the extract containing epitulipinolide and costunolide as active ingredients from the bark of *Liriodendron tulipifera* has been made for preventing or treating gastritis and/or stomach ulcer.

PREFERRED EMBODIMENT OF INVENTION

Figure 1:
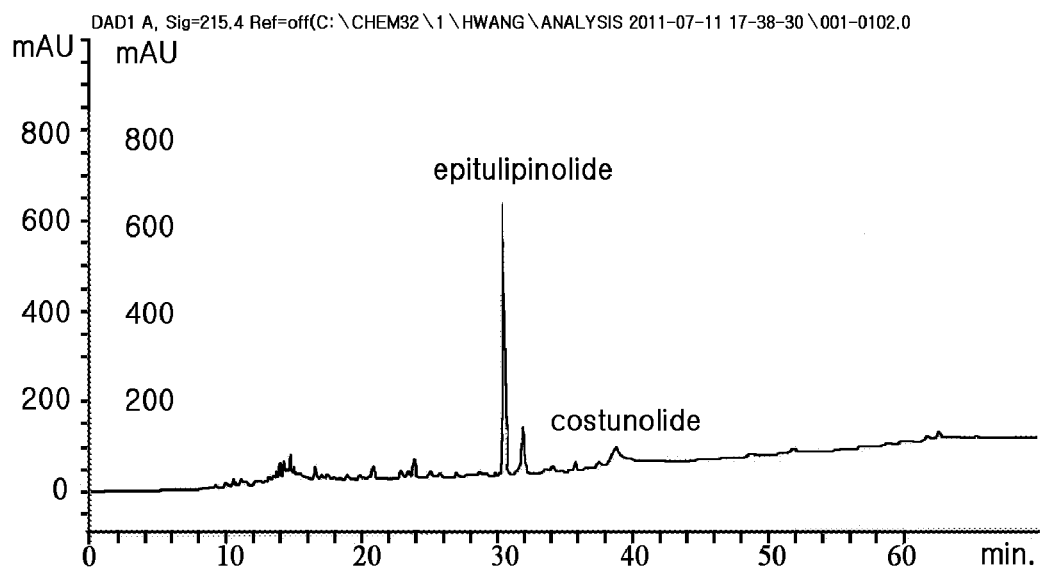
FIG. 1 shows liquid chromatography data of purified materials from the bark of *Liriodendron tulipifera* according to Preparation Example 9. Epitulipinolide and costunolide have been confirmed to be included.
Figure 2:
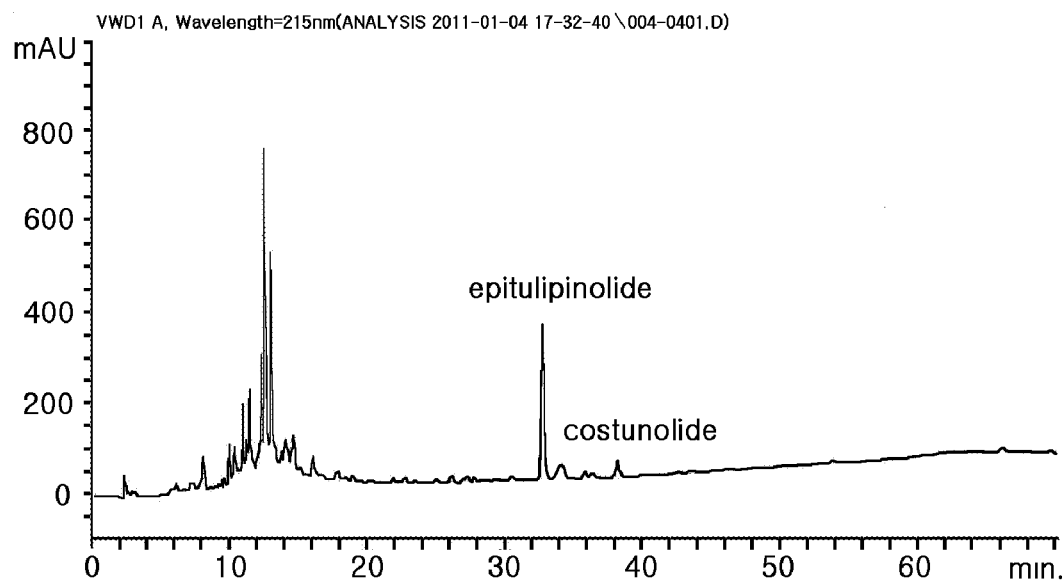
FIG. 2 shows liquid chromatography data of extract from the bark of *Liriodendron tulipifera* according to Preparation Example 1 before purification step. Epitulipinolide and costunolide have been confirmed to be included.
Figure 3:
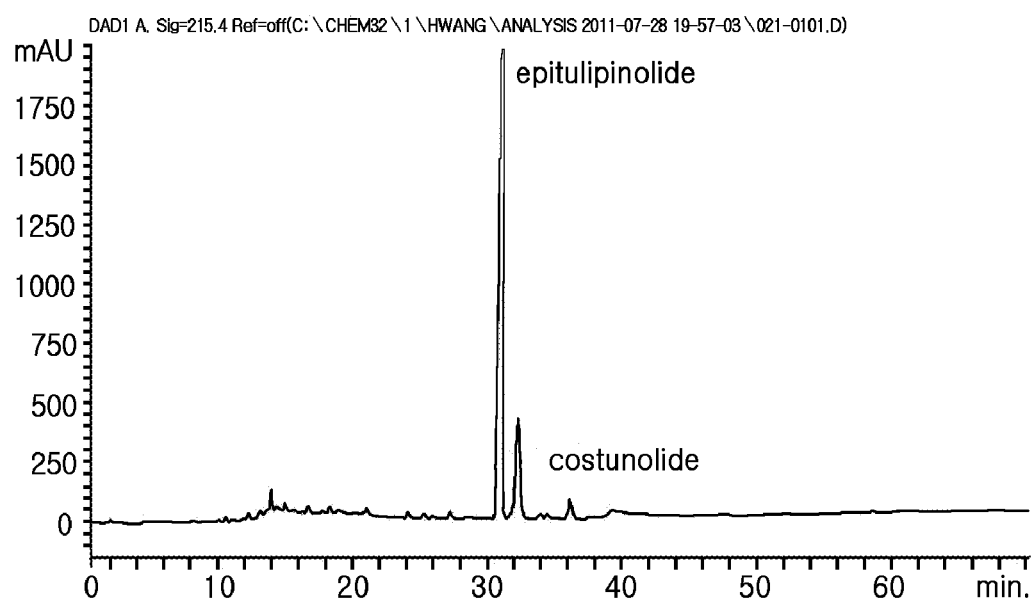
FIG. 3 shows liquid chromatography data of purified materials from the bark of *Liriodendron tulipifera* according to Preparation Example 11. Epitulipinolide and costunolide have been confirmed to be included.

The present application is to provide an extract from the bark of *Liriodendron tulipifera* containing epitulipinolide and costunolide.

Further, the present application is to provide a process for preparing the extract from the bark of *Liriodendron tulipifera*

Further, the present application is to provide an extract from the bark of *Liriodendron tulipifera* containing epitulipinolide and costunolide as well as a pharmaceutical composition for preventing or treating gastritis and/or stomach ulcer containing epitulipinolide and costunolide as active ingredients.

The extract from the bark of *Liriodendron tulipifera* has been prepared using the extraction solvent selected from ethyl acetate, dichloromethane, alcohol, alcohol aqueous solution and/or mixture of them. Further, epitulipinolide and costunolide have been included in this extract. Of course, epitulipinolide and costunolide have been used as component indicator of the extract from the bark of *Liriodendron tulipifera*.

Of course, the extract from the bark of *Liriodendron tulipifera* has an excellent efficacy for treating gastrointestinal disease. For measuring the efficacy for treating gastritis and/or stomach ulcer, various kinds of in vivo animal test models have been employed. For example, water-immersion-restraint stress model, HCl-EtOH inducing gastritis model and/or indomethacin inducing stomach ulcer model has been employed. As a result of test, the extract from the bark of *Liriodendron tulipifera* shows an excellent efficacy to the gastritis and/or stomach ulcer by promoting the prostaglandin biosynthesis.

On the other hand, the present invention provide a pharmaceutical composition from the bark of *Liriodendron tulipifera* comprising epitulipinolide and costunolide as active ingredients for preventing or treating gastrointestinal disease.

The preparation method of extract from the bark of *Liriodendron tulipifera* can be explained as follows.

The preparation method of present application comprises 2 preparation steps; (1) preparation step of extract from the bark of *Liriodendron tulipifera* using specific solvent of ethyl acetate or dichloromethane (Method 1), (2) purification step for obtaining purified material enhancing the amount of component indicator from the extract obtained in step 1 (Method 2).

In Method 1, after chopping and powdering the bark of *Liriodendron tulipifera*, the extraction has been carried out using extraction solvent selected from ethyl acetate or dichloromethane. After concentrating extract, the obtained material has contained epitulipinolide and costunolide as active ingredient.

In Method 2, the extract obtained in Method 1 has been dissolved using alcohol aqueous solution. After adding hexane, the lipid ingredient dissolved in hexane as well as water insoluble material have been removed. After separating alcohol aqueous solution layer, high purity of epitulipinolide and costunolide has been obtained. Further, said alcohol aqueous solution can be diluted into low concentration of alcohol aqueous solution by adding water. After adding dichloromethane to the obtained alcohol aqueous solution, epitulipinolide and costunolide can be isolated and purified in the dichloromethane fraction.

Obtained fraction according to Method 1 and Method 2 has been concentrated and dried. Finally, the extract composition can be made after removing remained solvent in the fraction

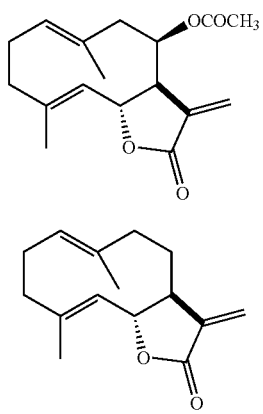

Formula 1

Formula 2

Therefore, the present invention provides a method for extracting and purifying epitulipinolide (formula 1) and costunolide (formula 2) from the bark of *Liriodendron tulipifera*.

The bark of *Liriodendron tulipifera* has been collected from the *Liriodendron tulipifera* located Jeollanam-do, gangjingun in Republic of Korea. After chopping and powdering the collected bark of *Liriodendron tulipifera*, extraction solvent has been added in a 2~20 times amount, preferably 4~10 times amount of collected bark. The extraction has been carried out for 24~96 hours at 15~50. Finally, the extract has been obtained after concentrating and drying it at reduced pressure.

The extract obtained from the bark of *Liriodendron tulipifera* has been analyzed for measuring epitulipinolide and costunolide amount using Agilent HPLC 1200 series (U.S.A.) according to high performance liquid chromatography method. The conditions for HPLC analysis are as follows. Reverse phase column Kromasil C18, 5 mg/ml of sample concentration, 215 nm of UV wave length (flow rate: 1.0 ml/min), mobile phase gradient condition has been shown in Table 1.

TABLE 1

| Mobile phase gradient condition for HPLC analysis | | |
|---|---|---|
| retention time(min.) | water (wt %) | methanol (wt %) |
| 0 | 98 | 2 |
| 10 | 50 | 50 |
| 60 | 0 | 100 |

TABLE 1-continued

| Mobile phase gradient condition for HPLC analysis | | |
|---|---|---|
| retention time(min.) | water (wt %) | methanol (wt %) |
| 70 | 0 | 100 |
| 80 | 98 | 2 |

As a result of HPLC analysis according to gradient condition as shown in Table 1, the main components of epitulipinolide and costunolide have been detected at 31 minute and at 36 minute of retention time respectively. Further, to confirm the presence of epitulipinolide and costunolide respectively, each retention time of the standard of epitulipinolide and the standard of costunolide has been measured as the same manner. Upon comparing the retention time between standard and obtained material, we have found that epitulipinolide and costunolide have been isolated and measured.

In the aspect of stereochemistry, the specific rotation of epitulipinolide has been measured. The measured value of epitulipinolide ($[\alpha]D=+74$) from the extract of *Liriodendron tulipifera* has almost corresponded with reported value of epitulipinolide ($[\alpha]D=\pm76$). Therefore, the presence of epitulipinolide has been confirmed by stereochemistry.

On the other hand, each molecular weight of epitulipinolide, costunolide and other components from the extract of *Liriodendron tulipifera* has been measured according to LC-MS. It has been confirmed that the molecular weight of epitulipinolide is 290, while the molecular weight of costunolide is 232. Further, other components, ridentin (Mw=264) and deacetyllipiferolide (Mw=264) have been also measured and confirmed.

LC-MS analysis instrument made by Waters has been employed using reverse phase column. 2 μl of sample volume concentration, 200-500 nm of UV wave length (flow rate: 0.3 ml/min), mobile phase gradient condition has been shown in Table 2.

TABLE 2

| Mobile phase gradient condition for LC-MS analysis | | |
|---|---|---|
| retention time(min.) | water (wt %) | ACN (wt %) |
| 0 | 85 | 15 |
| 10 | 30 | 70 |
| 60 | 0 | 100 |
| 70 | 0 | 100 |

Preparation step of extract from the bark of *Liriodendron tulipifera* using specific solvent of ethyl acetate or dichloromethane (Method 1) has been described as follows.

The preparation method of the extract from the bark of *Liriodendron tulipifera* comprises 1) mixing 1 wt part of chopped and dried bark of *Liriodendron tulipifera* with 2~20 wt part of ethyl acetate or dichloromethane; and 2) extracting and concentrating said mixture for 1~4 days at 15~50° C.

Further, said extract comprises 0.1~10 wt % of epitulipinolide and costunolide, while said extraction is made by at least one selected from enfleurage, percolation, ultra sonic, maceration or reflux.

The present application can be explained more concretely by following Preparation Examples and Comparative Preparation Examples. However, the scope of present application cannot be limited by following Preparation Examples.

In Preparation Examples 1~8, preparation Method 1 of the extract from the bark of *Liriodendron tulipifera* has been described. Further, it has been measured that the amount of epitulipinolide has been 3.1~9.7 wt % while the amount of costunolide has been 0.14~0.35 wt % in these Preparation Examples.

Preparation Example 1

Extract Obtained Using Ethyl Acetate 200 g of dried and chopped bark of *Liriodendron tulipifera* has been extracted using 800 ml of ethyl acetate at 50° C. for 24 hours. Obtained extracted mixture has been concentrated and dried at reduced pressure. Finally, 6.83 g of extract has been obtained. The amount of epitulipinolide has been 3.96 wt % and the amount of costunolide has been 0.18 wt %.

Preparation Example 2

Extract Obtained Using Ethyl Acetate 200 g of dried and chopped bark of *Liriodendron tulipifera* has been extracted using 800 ml of ethyl acetate at 50° C. for 48 hours. Obtained extracted mixture has been concentrated and dried at reduced pressure. Finally, 7.67 g of extract has been obtained. The amount of epitulipinolide has been 3.94 wt % and the amount of costunolide has been 0.14 wt %.

Preparation Example 3

Extract Obtained Using Ethyl Acetate 200 g of dried and chopped bark of *Liriodendron tulipifera* has been extracted using 800 ml of ethyl acetate at room temperature for 24 hours. Obtained extracted mixture has been concentrated and dried at reduced pressure. Finally, 3.10 g of extract has been obtained. The amount of epitulipinolide has been 3.19 wt % and the amount of costunolide has been 0.19 wt %.

Preparation Example 4

Extract Obtained Using Ethyl Acetate 200 g of dried and chopped bark of *Liriodendron tulipifera* has been extracted using 800 ml of ethyl acetate at room temperature for 48 hours. Obtained extracted mixture has been concentrated and dried at reduced pressure. Finally, 3.85 g of extract has been obtained. The amount of epitulipinolide has been 3.96 wt % and the amount of costunolide has been 0.20 wt %.

Preparation Example 5

Extract Obtained Using Dichloromethane 200 g of dried and chopped bark of *Liriodendron tulipifera* has been extracted using 800 ml of dichloromethane at 36° C. for 24 hours. Obtained extracted mixture has been concentrated and dried at reduced pressure. Finally, 3.79 g of extract has been obtained. The amount of epitulipinolide has been 4.48 wt % and the amount of costunolide has been 0.27 wt %.

Preparation Example 6

Extract Obtained Using Dichloromethane 200 g of dried and chopped bark of *Liriodendron tulipifera* has been extracted using 800 ml of dichloromethane at 36° C. for 72 hours. Obtained extracted mixture has been concentrated and dried at reduced pressure. Finally, 4.95 g of extract has been obtained. The amount of epitulipinolide has been 5.10 wt % and the amount of costunolide has been 0.35 wt %.

Preparation Example 7

Extract Obtained Using Dichloromethane 200 g of dried and powdered bark of *Liriodendron tulipifera* has been extracted using 800 ml of dichloromethane at 36° C. for 24 hours. Obtained extracted mixture has been concentrated and dried at reduced pressure. Finally, 9.12 g of extract has been obtained. The amount of epitulipinolide has been 9.11 wt % and the amount of costunolide has been 0.29 wt %.

Preparation Example 8

Extract Obtained Using Dichloromethane 200 g of dried and powdered bark of *Liriodendron tulipifera* has been extracted using 800 ml of dichloromethane at 36° C. for 72 hours. Obtained extracted mixture has been concentrated and dried at reduced pressure. Finally, 8.58 g of extract has been obtained. The amount of epitulipinolide has been 9.65 wt % and the amount of costunolide has been 0.31 wt %.

In Comparative Preparation Examples 1~6, the corresponding method for comparison of preparation Method 1 of present invention has been described. Further, it has been measured that the amount of epitulipinolide has been 1.28~1.97 wt % while the amount of costunolide has been 0.08~0.18 wt % in these Comparative Preparation Examples, the amount of which has been comparatively lower than that of Preparation Example.

Comparative Preparation Example 1

Extract Obtained Using Ethanol 200 g of dried and chopped bark of *Liriodendron tulipifera* has been extracted using 800 ml of 95% ethanol at 70° C. for 24 hours. Obtained extracted mixture has been concentrated and dried at reduced pressure. Finally, 14.87 g of extract has been obtained. The amount of epitulipinolide has been 1.28 wt % and the amount of costunolide has been 0.08 wt %.

Comparative Preparation Example 2

Extract Obtained Using Ethanol 200 g of dried and chopped bark of *Liriodendron tulipifera* has been extracted using 800 ml of 95% ethanol at 70° C. for 72 hours. Obtained extracted mixture has been concentrated and dried at reduced pressure. Finally, 17.78 g of extract has been obtained. The amount of epitulipinolide has been 1.63 wt % and the amount of costunolide has been 0.15 wt %.

Comparative Preparation Example 3

Extract Obtained Using Isopropanol 200 g of dried and chopped bark of *Liriodendron tulipifera* has been extracted using 800 ml of isopropanol at 70° C. for 24 hours. Obtained extracted mixture has been concentrated and dried at reduced pressure. Finally, 3.10 g of extract has been obtained. The amount of epitulipinolide has been 1.75 wt % and the amount of costunolide has been 0.10 wt %.

Comparative Preparation Example 4

Extract Obtained Using Isopropanol 200 g of dried and chopped bark of *Liriodendron tulipifera* has been extracted using 800 ml of isopropanol at 70° C. for 72 hours. Obtained extracted mixture has been concentrated and dried at reduced pressure. Finally, 4.10 g of extract has been obtained. The amount of epitulipinolide has been 1.97 wt % and the amount of costunolide has been 0.17 wt %.

Comparative Preparation Example 5

Extract Obtained Using Buthanol 200 g of dried and chopped bark of *Liriodendron tulipifera* has been extracted using 800 ml of buthanol at 70° C. for 24 hours. Obtained extracted mixture has been concentrated and dried at reduced pressure. Finally, 2.85 g of extract has been obtained. The amount of epitulipinolide has been 1.80 wt % and the amount of costunolide has been 0.13 wt %.

Comparative Preparation Example 6

Extract Obtained Using Buthanol 200 g of dried and chopped bark of *Liriodendron tulipifera* has been extracted using 800 ml of buthanol at 70° C. for 72 hours. Obtained extracted mixture has been concentrated and dried at reduced pressure. Finally, 3.40 g of extract has been obtained. The amount of epitulipinolide has been 1.57 wt % and the amount of costunolide has been 0.17 wt %.

TABLE 3

The amount of epitulipinolide and costunolide in the extract

|  | epitulipinolide | costunolide |
| --- | --- | --- |
| Prep. Example 1 | 3.96% | 0.18% |
| Prep. Example 2 | 3.94% | 0.14% |
| Prep. Example 3 | 3.19% | 0.19% |
| Prep. Example 4 | 3.96% | 0.20% |
| Prep. Example 5 | 4.48% | 0.27% |
| Prep. Example 6 | 5.10% | 0.35% |
| Prep. Example 7 | 9.11% | 0.29% |
| Prep. Example 8 | 9.65% | 0.31% |
| Com. Prep. Example 1 | 1.28% | 0.08% |
| Com. Prep. Example 2 | 1.63% | 0.15% |
| Com. Prep. Example 3 | 1.75% | 0.10% |
| Com. Prep. Example 4 | 1.97% | 0.17% |
| Com. Prep. Example 5 | 1.80% | 0.13% |
| Com. Prep. Example 6 | 1.57% | 0.17% |

As shown in Table 3, the amount of epitulipinolide in the extract from the bark of *Liriodendron tulipifera* according to the method disclosed in Preparation Example has been 3.1~9.7%, whereas the amount of epitulipinolide in the extract from the bark of *Liriodendron tulipifera* according to the method disclosed in Comparative Preparation Example has been 1.28~1.97%, the amount of which has been comparatively lower than that of Preparation Example. The difference of amount has been resulted from the difference of extraction solvent. As a result, it has been measured that ethyl acetate or dichloromethane has been useful for extraction solvent compared to alcohol solvent, such as, ethanol, isopropanol or buthanol.

Purification step for obtaining purified material enhancing the amount of component indicator from the extract obtained in step 1 (Method 2) has been described as follows.

Purification step has comprised the steps of: 1) dissolving the extract obtained in Method 1 with C1~C3 lower alcohol aqueous solution; 2) removing the lipid and water-insoluble material in the hexane layer, after adding and mixing hexane to the mixture obtained in step 1); and 3) isolating, purifying and drying the material in lower alcohol aqueous solution layer.

Further, said step 2) has additionally comprised the step for adding water to the lower alcohol aqueous solution layer to obtain the low concentration of lower alcohol aqueous solution; the step for adding dichloromethane to obtain dichloromethane layer; and the step for isolating, purifying and drying the material in dichloromethane layer.

In following Preparation Examples 9~12, the purification methods of extract obtained in Preparation Examples 1, 2, 6, 7 have been described.

Preparation Example 9

Purification of Extract 1 g of extract obtained in Preparation Example 1 has been dissolved with 50 ml of 70% ethanol. After adding 50 ml of hexane, the mixture has been agitated and fractioned. Obtained 70% ethanol fraction has been isolated and dried. Finally, 0.483 g of purified extract has been obtained. The amount of epitulipinolide has been 9.72 wt % and the amount of costunolide has been 0.28 wt %.

Preparation Example 10

Purification of Extract 1 g of extract obtained in Preparation Example 2 has been dissolved with 50 ml of 70% ethanol. After adding 50 ml of hexane, the mixture has been agitated and fractioned. Obtained 70% ethanol fraction has been isolated and dried. Finally, 0.571 g of purified extract has been obtained. The amount of epitulipinolide has been 10.94 wt % and the amount of costunolide has been 0.30 wt %.

Preparation Example 11

Purification of Extract 1 g of extract obtained in Preparation Example 6 has been dissolved with 50 ml of 70% ethanol. After adding 50 ml of hexane, the mixture has been agitated and fractioned. After obtaining ethanol fraction, 40 ml of water and 90 ml of dichloromethane have been added and agitated. Obtained dichloromethane fraction has been isolated and dried. Finally, 0.071 g of purified extract has been obtained. The amount of epitulipinolide has been 23.43 wt % and the amount of costunolide has been 0.79 wt %.

Preparation Example 12

Purification of Extract 1 g of extract obtained in Preparation Example 7 has been dissolved with 50 ml of 70% ethanol. After adding 50 ml of hexane, the mixture has been agitated and fractioned. After obtaining ethanol fraction, 40 ml of water and 90 ml of dichloromethane have been added and agitated. Obtained dichloromethane fraction has been isolated and dried. Finally, 0.069 g of purified extract has been obtained. The amount of epitulipinolide has been 21.19 wt % and the amount of costunolide has been 0.94 wt %.

TABLE 4

The amount of epitulipinolide and costunolide

| | epitulipinolide | costunolide |
|---|---|---|
| Prep. Example 9 | 9.72% | 0.28% |
| Prep. Example 10 | 10.94% | 0.30% |
| Prep. Example 11 | 23.43% | 0.79% |
| Prep. Example 12 | 21.19% | 0.94% |

As shown in Table 4, the amount and concentration of epitulipinolide and costunolide has been enhanced according to the Method 2 of present invention compared to that of Preparation Examples 1, 2, 6, 7. Therefore, purification step can enhance the concentration of epitulipinolide and costunolide in the extract from the bark of *Liriodendron tulipifera*.

What is claimed is:

1. A process for preparing an extract from the bark of *Liriodendron tulipifera* comprising the steps of:
   a) mixing 1 weight part of chopped and dried bark of *Liriodendron tulipifera* with 2 to 20 weights part of ethyl acetate or dichloromethane to form a mixture; and
   b) extracting and concentrating said mixture for 1 to 4 days at a temperature of 15° C. to 50° C. to form the extract of the bark of *Liriodendron tulipifera*,
      wherein said extract comprises 0.1 to 10 weight of epitulipinolide and costunolide, and
      wherein said extraction is made by at least one technique selected from the group consisting of: enfleurage, percolation, ultra sonic, maceration and reflux.

2. The process of claim 1, further comprising the steps of:
   a) dissolving the extract of the bark of *Liriodendron tulipifera* obtained in step b) of claim 1 with a C1-C3 lower alcohol aqueous solution;
   b) adding hexane to form a hexane layer and a C1-C3 lower alcohol aqueous solution layer;
   c) removing the hexane layer containing lipid and water-insoluble material, and
   d) concentrating the C1-C3 lower alcohol aqueous solution layer and drying the material obtained thereof.

* * * * *